US010869663B2

(12) United States Patent
Shelton, IV et al.

(10) Patent No.: US 10,869,663 B2
(45) Date of Patent: Dec. 22, 2020

(54) END EFFECTOR CONFIGURED TO MATE WITH ADJUNCT MATERIALS

(71) Applicant: Ethicon LLC, Guaynabo, PR (US)

(72) Inventors: Frederick E. Shelton, IV, Hillsboro, OH (US); Jason L. Harris, Lebanon, OH (US); Prudence Vulhop, Cincinnati, OH (US); Michael J. Vendely, Lebanon, OH (US); Greg Scott, Cincinnati, OH (US); Kevin Weadock, Hillsborough, NJ (US); Michael Cardinale, Morristown, NJ (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 549 days.

(21) Appl. No.: 15/436,208

(22) Filed: Feb. 17, 2017

(65) Prior Publication Data

US 2018/0235616 A1 Aug. 23, 2018

(51) Int. Cl.
*A61B 17/072* (2006.01)
*A61B 17/29* (2006.01)

(52) U.S. Cl.
CPC ...... *A61B 17/072* (2013.01); *A61B 17/07207* (2013.01); *A61B 17/07292* (2013.01); *A61B 17/29* (2013.01); *A61B 2017/07264* (2013.01); *A61B 2017/07271* (2013.01)

(58) Field of Classification Search
CPC ...... A61B 17/027207; A61B 17/07292; A61B 17/29; A61B 17/072
USPC ..................................................... 227/178.1
See application file for complete search history.

(56) References Cited

U.S. PATENT DOCUMENTS

| 7,143,925 | B2 | 12/2006 | Shelton, IV et al. |
| 7,601,118 | B2 | 10/2009 | Smith et al. |
| 8,317,070 | B2 | 11/2012 | Hueil et al. |
| 8,393,514 | B2 | 3/2013 | Shelton, IV et al. |
| 9,282,962 | B2 | 3/2016 | Schmid et al. |

(Continued)

FOREIGN PATENT DOCUMENTS

EP 2644126 A2 10/2013

OTHER PUBLICATIONS

Extended European Search Report fo EP App. No. 18157137.3 dated May 2, 2018 (8 pages).

*Primary Examiner* — Michelle Lopez
*Assistant Examiner* — Chinyere J Rushing-Tucker
(74) *Attorney, Agent, or Firm* — Mintz Levin Cohn Ferris Glovsky and Popeo, P.C.

(57) ABSTRACT

An adjunct material for use with an end effector in a surgical instrument is provided that has at least one projection configured to mate with a corresponding recess formed in at least one jaw, such as a cartridge or anvil, of the end effector. The at least one projection can be one or more discrete projections or longitudinal projection(s) extending between distal and proximal ends of the adjunct material. An applicator member can be used to apply force to the adjunct material to thus cause the adjunct material to mate with the jaw of the end effector. The applicator member can be configured told the adjunct material and can be clamped between the jaws of the end effector to release the adjunct material onto the jaw. Also, an applicator member can be used to push portions of an adjunct material into corresponding recesses in a jaw.

21 Claims, 13 Drawing Sheets

(56) References Cited

U.S. PATENT DOCUMENTS

| | | |
|---|---|---|
| 10,307,160 B2 | 6/2019 | Vendely et al. |
| 2009/0001122 A1* | 1/2009 | Prommersberger ........................ A61B 17/07207 227/176.1 |
| 2012/0241492 A1 | 9/2012 | Shelton, IV et al. |
| 2012/0241503 A1 | 9/2012 | Baxter, III et al. |
| 2012/0253298 A1* | 10/2012 | Henderson ....... A61B 17/00491 604/288.04 |
| 2013/0161374 A1* | 6/2013 | Swayze ................ A61B 17/068 227/176.1 |
| 2013/0221065 A1 | 8/2013 | Aronhalt et al. |
| 2013/0256377 A1 | 10/2013 | Schmid et al. |
| 2014/0224686 A1* | 8/2014 | Aronhalt ............. A61B 17/068 206/339 |
| 2015/0122872 A1* | 5/2015 | Olson .............. A61B 17/07292 227/179.1 |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0272575 A1 | 10/2015 | Leimbach et al. |
| 2015/0277471 A1 | 10/2015 | Leimbach et al. |
| 2015/0351758 A1 | 12/2015 | Shelton, IV et al. |
| 2016/0089142 A1 | 3/2016 | Harris et al. |
| 2016/0278764 A1* | 9/2016 | Shelton, IV ......... A61B 17/068 |
| 2016/0278774 A1 | 9/2016 | Shelton, IV et al. |
| 2017/0055986 A1 | 3/2017 | Harris et al. |
| 2017/0086838 A1 | 3/2017 | Harris et al. |

* cited by examiner

END EFFECTOR CONFIGURED TO MATE WITH ADJUNCT MATERIALS

FIELD

The present disclosure relates generally to adjunct materials used in conjunction with an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

In one aspect, an end effector for a surgical instrument is provided that in some embodiments includes a first jaw, a second jaw, and at least one recess formed in at least one jaw of the first and second jaws. The first jaw has a cartridge with a plurality of staple cavities configured to seat staples therein, the staple cavities opening on a tissue-facing surface of the cartridge. The second jaw opposing the first jaw has an anvil with a plurality of staple forming cavities formed on a tissue-facing surface thereof. The first and second jaws are configured to clamp tissue therebetween. The end effector includes an adjunct material having at least one projection configured to mate with the at least one recess to retain the adjunct material on the at least one jaw, the at least one projection being disposed at least at proximal and distal ends of the adjunct material. The end effector also includes a removable applicator member configured to apply force to the adjunct material so as to cause the at least one projection of the adjunct to be received in a corresponding recess formed in the at least one jaw to thereby cause the adjunct material to be releasably mated with the at least one jaw.

The end effector can vary in any of various ways. For example, the at least one projection can be in the form of at least one first discrete projection formed at a distal end of the adjunct material and at least one second discrete projection formed at a proximal of the adjunct material, wherein the at least one recess formed in the at least one jaw is in the form of a first recess formed at a distal end of the at least one jaw and a second recess formed at a proximal end of the at least one jaw.

The applicator member can have a variety of configurations. For example, the applicator member can be removably coupled to the at least one jaw. In some embodiments, the applicator member can be configured to releasably hold the adjunct material so as to release the adjunct material when the applicator member is clamped between the first and second jaws. In some embodiments, the applicator member can include at least one applicator member projection facing the adjunct material and formed on the applicator member at a location thereof corresponding to a location of the at least one projection of the adjunct material. When the applicator member is configured to apply the force to the adjunct material, the at least one applicator member projection is configured to cause the at least one projection of the adjunct material to be at least partially received in the at least one recess.

In some embodiments, the end effector further includes a polymer attachment layer configured to be positioned between the at least one jaw and the adjunct material, the polymer attachment layer including at least one second projection facing the adjunct material and formed on the polymer attachment layer at a location thereof corresponding to a location of the at least one projection of the adjunct material. When the applicator member is configured to apply the force to the adjunct material and to the polymer attachment layer positioned between the at least one jaw and the adjunct material, the at least one applicator member projection is configured to cause the at least one projection of the adjunct material and the at least one second projection of the polymer material to be at least partially received in the at least one recess.

In some embodiments, the at least one projection of the adjunct material includes or is in the form of a first longitudinal projection formed on one side of the adjunct material and a second longitudinal projection formed on another, opposite side of the adjunct material, the first and second longitudinal projections extending between distal and proximal ends of the adjunct material.

In some embodiments, at least one of the first and second longitudinal projections can have a mating feature formed thereon that is configured to be at received within a corresponding recess of the at least one recess. The at least one longitudinal projection can be formed from at least partially flexible material such that, as the at least one longitudinal projection is received within a corresponding recess, the longitudinal projection is contracted due to the force being applied by the applicator member and then expanded to be fittingly received within the recess.

In some embodiments, the at least one projection formed on the adjunct material includes or is in the form of a plurality of discrete projections formed from an at least partially flowable material and having a changeable configuration such that, when the applicator member applies the force to the adjunct material to cause each of the discrete projections to be at least partially received within a corresponding recess in the at least one jaw, the configuration of each discrete projection that is at least partially received within the corresponding recess changes to conform to a configuration of the corresponding recess. Each of the discrete projections is configured to separate from the adjunct material and remain within the recess after the staples are formed against the staple forming cavities to apply the adjunct material to a tissue clamped between the first and second jaws.

In another aspect, an end effector for a surgical instrument is provided that in some embodiments includes a first jaw, a second jaw, a plurality of recesses formed in at least one jaw of the first and second jaws, an adjunct material formed from at least partially stretchable material, and an applicator member. The first jaw has a cartridge with a plurality of staple cavities configured to seat staples therein, the staple cavities opening on a tissue-facing surface of the cartridge. The second jaw opposing the first jaw has an anvil with a plurality of staple forming cavities formed on a tissue-facing surface thereof. The first and second jaws are configured to clamp tissue therebetween. The applicator member has a plurality of projections, each of the plurality of projections being configured to mate with a corresponding recess in the at least one jaw, and the applicator member is configured to apply force to the adjunct material so as to cause each projection formed on the applicator member to be received in a corresponding recess formed in the at least one jaw to thereby cause a portion the adjunct material disposed between the at least one jaw and the applicator member to be releasably retained in the corresponding recess in the at least one jaw.

The end effector can vary in any of various ways. For example, at least one of the plurality of recesses formed in the at least one jaw can have at least one retaining feature configured to releasably retain the portion of the adjunct material in the corresponding recess.

BRIEF DESCRIPTION OF DRAWINGS

This disclosure will be more fully understood from the following detailed description taken in conjunction with the accompanying drawings, in which.

DETAILED DESCRIPTION

Figure 1:
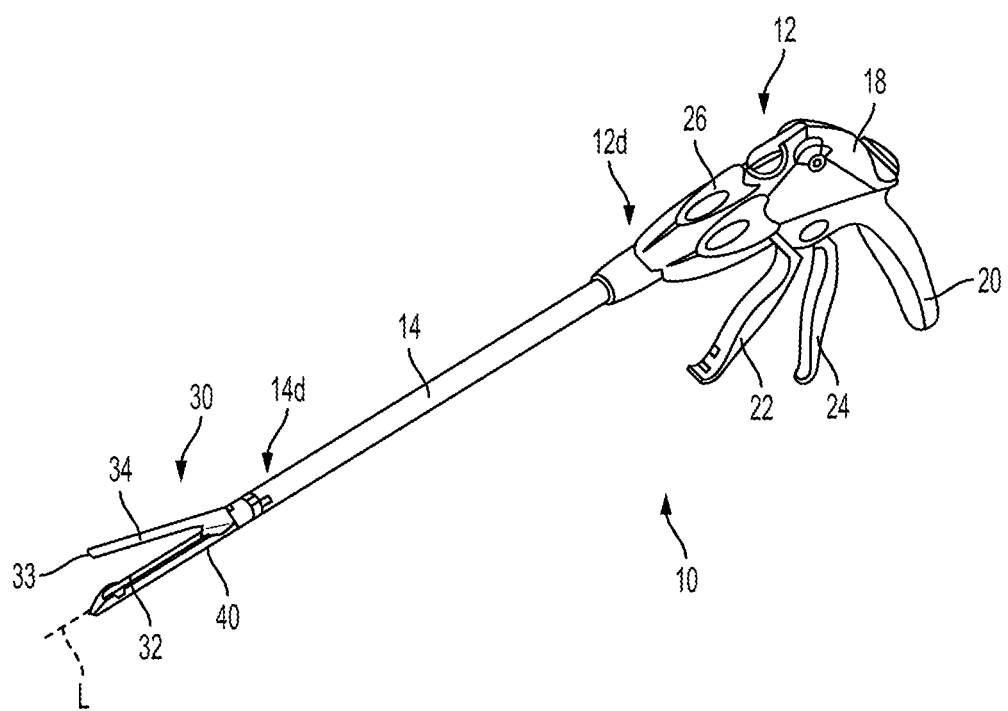
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example, linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
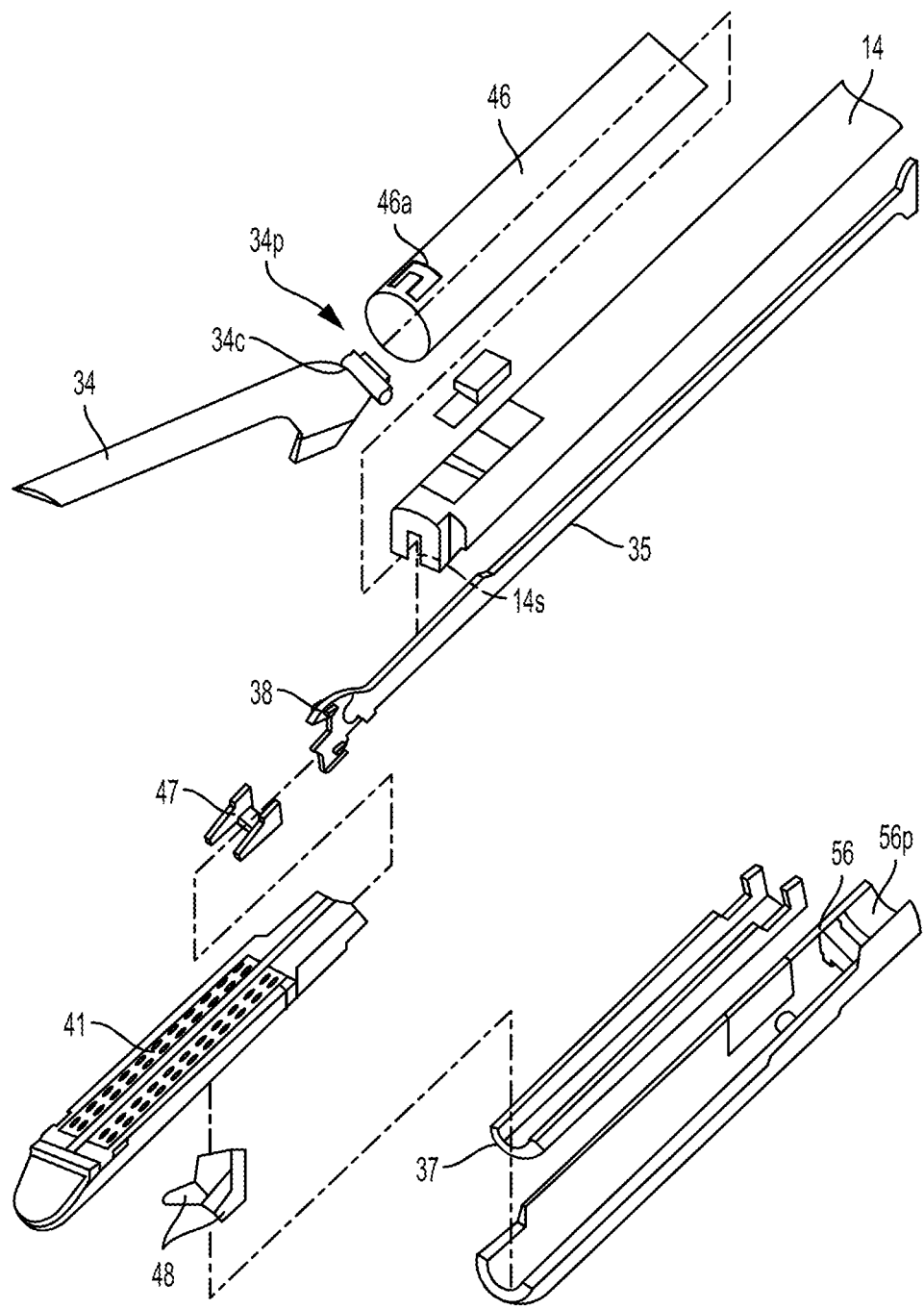
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. (Movable about a hinge and can also be rotationally moved about the axis of the shaft) Components of a firing system (number?) can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
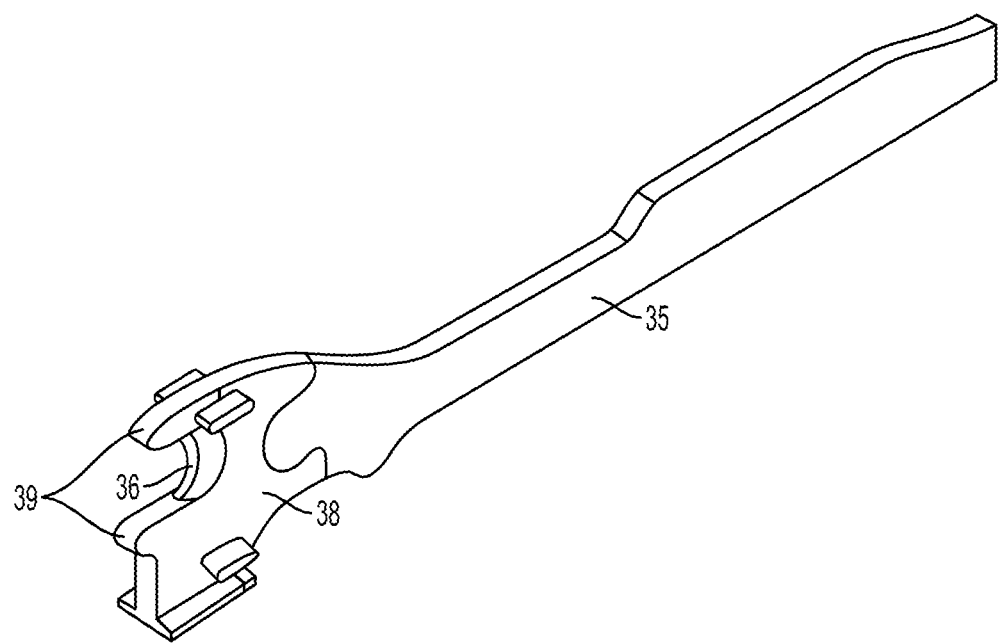
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
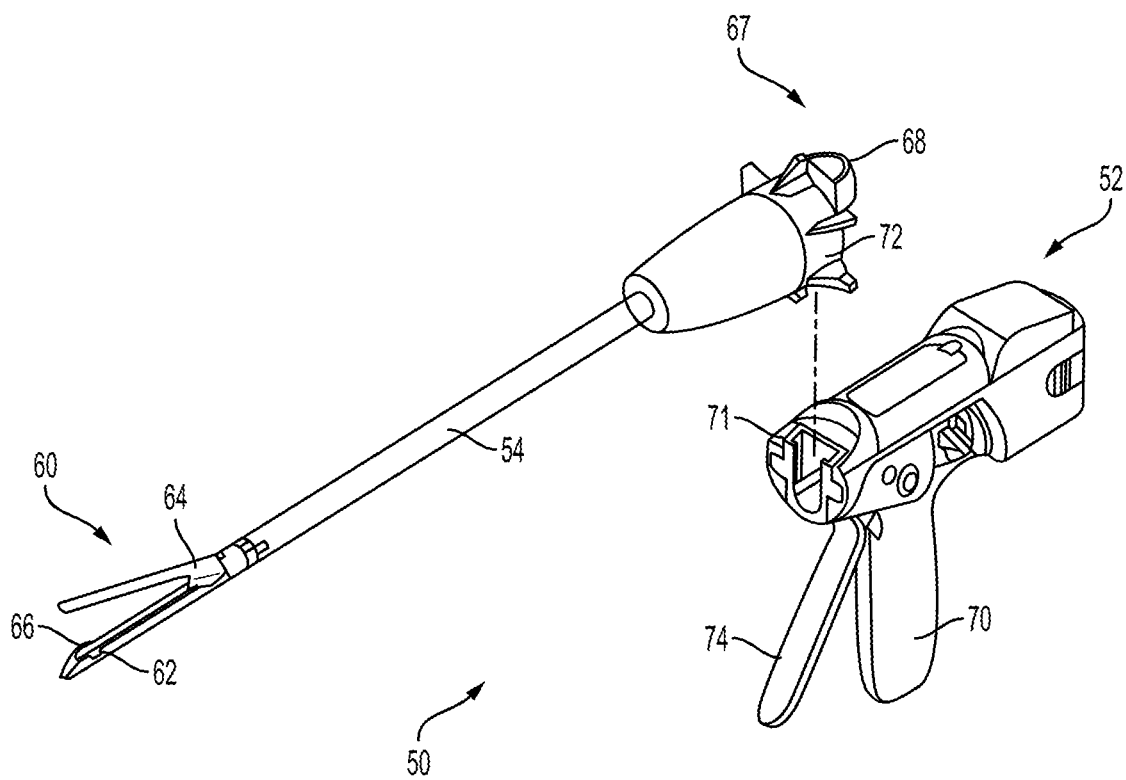
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
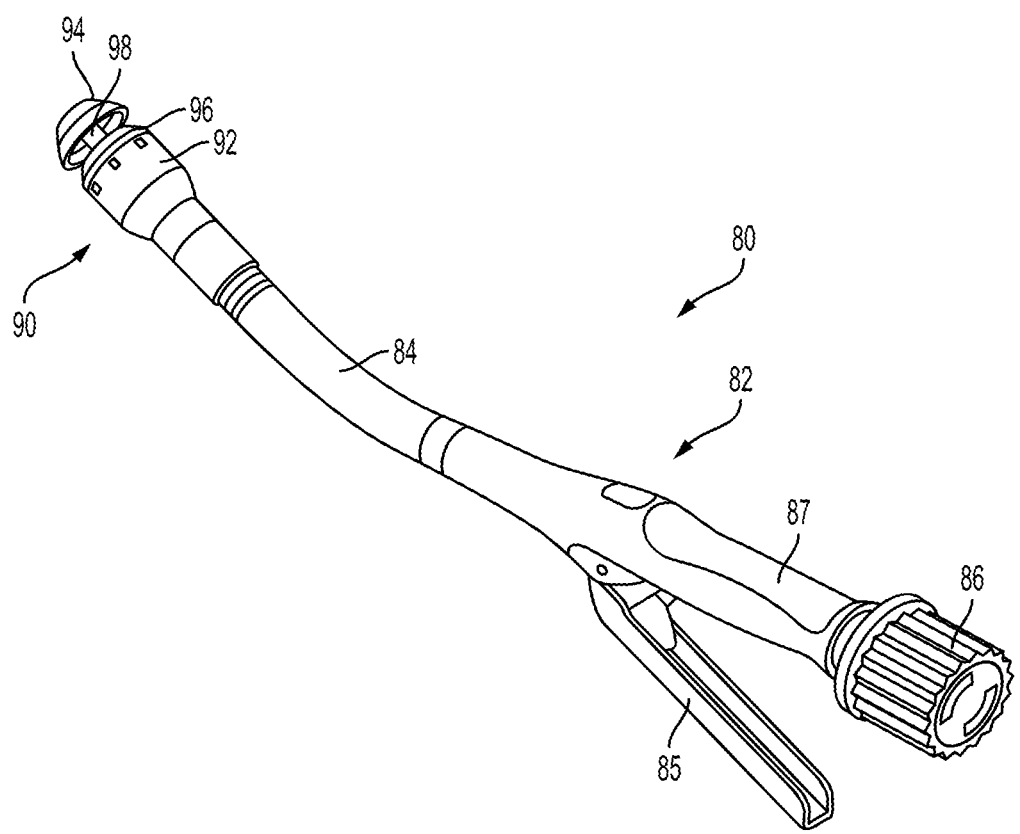
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or a combination of materials discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjuncts that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementations

In some implementations, an adjunct material is configured to be releasably retained on a jaw of an end effector for a surgical instrument using complementary mating features formed on the jaw and on the adjunct. In particular, the adjunct material can have discrete or longitudinal projections formed thereon at least at distal and proximal ends of the adjunct material. The projections are configured to be received within the complementary recesses formed in a jaw of the end effector to thereby releasably mate the adjunct material with the jaw. In some embodiments, the end effector can include an attachment feature in the form of a polymer attachment layer that can be used to attach the adjunct material to the jaw.

Furthermore, the end effector includes a removable applicator member configured to apply force to the adjunct material to cause the adjunct material to be releasably retained on the jaw. The applicator member can be in the form of an applicator or retainer removably coupled to the end effector, or in the form of a frame-like applicator configured to releasably hold the adjunct material, or in other forms. Thus, in some implementations, in use, the applicator member is removably coupled to the end effector and used to apply force to the adjunct material (and in some embodiments to a polymer attachment layer) to cause the projections of the adjunct material (and in some embodiments projections formed on the polymer attachment layer) to be at least partially received within corresponding recesses formed in the jaw. In other implementations, a frame-like applicator member holding at least one adjunct material is clamped between the jaws of the end effector. In this way, force is applied to the applicator member, which causes the applicator member to release the at least one adjunct material and to transfer the at least one adjunct material to at least one respective jaw of the end effector. After use, the applicator member can be separated from the end effector.

The described techniques can also employ other ways and structures to releasably retain an adjunct material on at least one jaw of an end effector of a surgical instrument.

Figure 6:
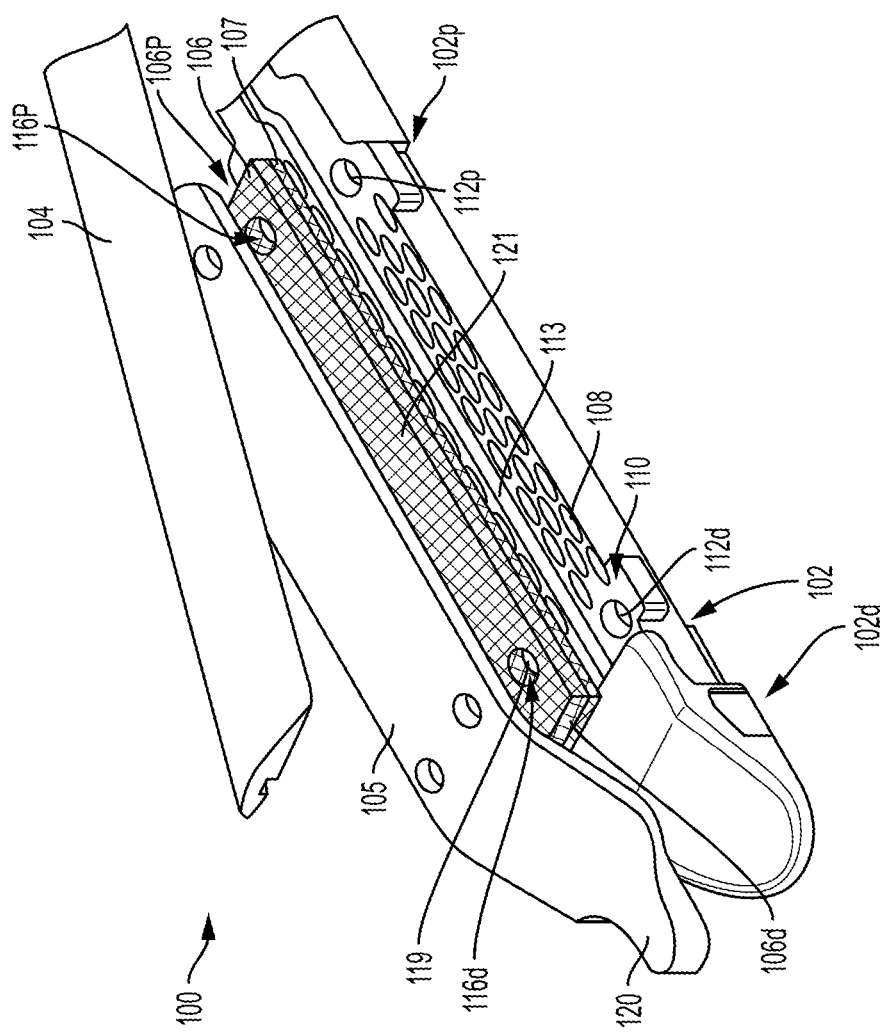
FIG. 6 is a perspective, partially exploded view of an end effector having an adjunct material releasably mounted thereon in accordance with the described techniques.
Figure 7:
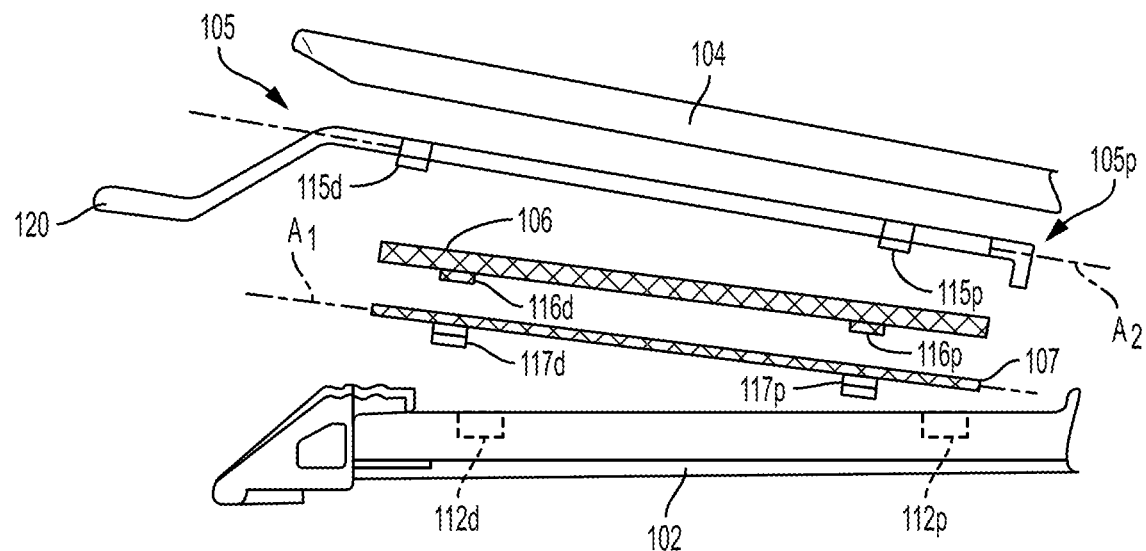
FIG. 7 is a partially exploded side view of the end effector of FIG. 6.

FIGS. 6-8 illustrate an example of an end effector 100 configured to releasably retain an adjunct material on one or both of its first and second opposed jaws configured to clamp tissue therebetween, in accordance with the described techniques. The end effector 100, partially illustrated in FIGS. 6 and 7, has a first jaw having a cartridge body 102 and a second jaw having an anvil 104. The cartridge body 102 is configured to releasably retain thereon an implantable adjunct material 106. The end effector 100 can be coupled to a distal end of a shaft of the surgical instrument (not shown). The end effector 100 can be used in any suitable surgical instrument, for example, a linear surgical stapler (e.g., stapler 10 in FIG. 1, stapler 50 in FIG. 4, or any other surgical stapler) which can be suitable for use with at least one adjunct.

As shown in FIG. 6, the cartridge body 102 has a plurality of staple-holding cavities 108 configured to seat staples therein, the staple-holding cavities 108 opening on a tissue-facing surface 110 of the cartridge 102. The staple cavities 108 form a certain pattern on the surface of the cartridge 102 which corresponds to a pattern of staple-forming cavities (obscured in FIG. 6) formed in the anvil 104. The cartridge body 102, also referred to as a cartridge, includes a cutting element channel 113 extending between distal and proximal ends 102d, 102p of the cartridge 102. The knife channel 113 is configured to receive a cutting element (e.g., a knife) as it moves distally therethrough. As shown in FIG. 6, the staple cavities 108 can form three rows on both sides of the cutting element channel 113, though it should be appreciated that the staple cavities 108 can form any other patterns on the tissue-facing surface 110.

The cartridge body 102 can be in the form of a staple channel configured to support a staple cartridge, which can be removably and replaceably seated within the staple channel. Furthermore, in some embodiments, the cartridge 102 can be part of a disposable loading unit coupled distally to a shaft of a surgical instrument.

The end effector 100 has the implantable adjunct material (or "adjunct") releasably mounted on one or both of the cartridge 102 and the anvil 104. In the illustrated implementation, the adjunct material 106 releasably retained on the cartridge 102 is discussed, though it should be appreciated that the anvil 104 can also have an adjunct material releasably retained thereon. As shown in FIGS. 6 and 7, the end effector also includes a loading member 105 configured to apply force to the adjunct material 106 to cause the adjunct material 106 to be retained on the cartridge 102, as discussed in more detail below. As also shown in FIGS. 6 and 7, and additionally illustrated in FIG. 8, the end effector 100 can further include a polymer attachment layer 107 configured to be positioned between the cartridge 102 and the adjunct material 106, as also discussed in more detail below.

In the illustrated implementation, the cartridge 102 can have at least one recess formed therein that opens on its tissue-facing surface 110, with the at least one recess being configured to mate with a respective projection formed in the adjunct 106. Thus, as shown in FIGS. 6 and 7, the cartridge 102 has at least one first recess 112d formed at the distal end 102d thereof and at least one second recess 112p formed at the proximal end 102p thereof. In the example illustrated, some of the recesses are obscured by the adjunct 106, and the at least one first recess 112d is in the form of two recesses formed on opposite sides of the cutting element channel 113. The at least one second recess 112p is similarly in the form of two recesses formed on opposite sides of the cutting element channel 113.

The recesses 112d, 112p formed in the cartridge 102 can have a variety of different configurations. In the illustrated example, as shown in FIG. 6, each of the recesses is a discrete recess that has a generally circular top cross-section such that the recess is cylindrical. It should be appreciated, however, that the recesses in the end effector's jaw, such as the cartridge, can have other configurations. For example, the recesses can be square, rectangular, semi-circular (e.g., having a semi-circular or oval shape as viewed from the top), and/or they can have any other suitable regular or irregular shapes. Regardless of their specific configuration(s), the recesses formed in the cartridge are configured to receive therein at least a portion of a respective projection formed on an adjunct material or another member, as discussed below.

As shown in FIG. 7, the adjunct material 106 has projections that are complementary to the recesses 112d, 112p formed in the cartridge 102 and that are configured to mate with the recesses 112d, 112p to retain the adjunct material 106 on the cartridge 102. In the illustrated embodiments, the adjunct material's projection(s) are disposed at least at proximal and distal ends of the adjunct material. In particular, as shown in FIG. 7, the adjunct material 106 has at least one first projection 116d formed at the distal end 106d thereof and at least one second projection 116p formed at the proximal end 106p thereof. In the example illustrated, where some of the projections are obscured, the at least one first projection 116d and the at least one second projection 116p are each in the form of two respective projections.

The adjunct material 106 can be formed from any suitable material or a combination of materials, which are discussed above. In some embodiments, the adjunct material 106 can have a thickness from about 0.004 inches to about 0.160 inches. In some embodiments, the adjunct material 106 can have a thickness from about 0.006 inches to about 0.008 inches. The projections 116d, 116p can have a height or thickness from about 0.005 to about 0.010 inches. In some embodiments, the projections, which can be formed from an elastomeric material, can have a height in a range from about 0.005 inches to about 0.015 inches, in a range from about 0.003 inches to about 0.006 inches, or a height that varies in other ranges. However, in some embodiments, the projections 116d, 116p can have a height or thickness up to about 0.180 inches or greater.

The locations of the first projections 116d and the second projections 116p formed on the adjunct material 106 correspond to the locations of the first recesses 112d and the second recesses 112p formed on the cartridge 102, respectively. However, in some embodiments, as discussed below, the first distal projections 116d can be closer to one another than the first distal recesses 112d, and similarly the second proximal projections 116p can be closer to one another than the second proximal recesses 112d. Furthermore, the configuration and size of the projections 116d, 116p corresponds to those of the recesses 112d, 112p. In this way, the projections 116d, 116p can be caused to be at least partially received within the recesses 112d, 112p, respectively.

For example, as shown in FIG. 6, the projections 116d, 116p configured to be at least partially received in the recesses 112d, 112p are complementary in shape to the recesses such that the projections 116d, 116p each have a generally circular top cross-section and are generally cylindrical. Furthermore, in the example of FIG. 6, the projections 116d, 116p are formed in the adjunct material 106 such they have an open-end channel extending least partially therethrough that opens on a side 121 of the adjunct material 106 opposed to its side facing the cartridge 102. For example, the projection 116d, which can represent all of the projections formed on the adjunct material 106, is shown to have a channel 119 extending therethrough. The channel 119 can be formed through the entire projection or through a portion thereof such that a recess can be formed on the side 121. Moreover, in some implementations, the projections 116d, 116p formed in the adjunct material 106 may not have a channel extending at least partially therethrough.

As mentioned above, in addition to the adjunct material 106, the end effector 100 of the illustrated implementation includes the polymer attachment layer 107 used in conjunction with the adjunct material 106. In particular, the polymer attachment layer 107 is disposed between the cartridge 102 and the adjunct material 106, as shown in FIGS. 6 and 7. The polymer attachment layer 107, which can be made from a pressure-sensitive adhesive or other suitable material, is used as an attachment or retaining feature. For example, non-limiting examples of materials can include materials described in U.S. Pat. Pub. No. 2016/0278774 entitled "Method of Applying a Buttress to a Surgical Stapler," filed on Mar. 25, 2015, which is hereby incorporated by reference herein in its entirety. The polymer attachment layer 107 is configured to hold the adjunct material 106 in a releasable engagement with the cartridge 102. Also, the polymer attachment layer 107 can provide additional reinforcement to a treatment site. The polymer material 107 can have a size that is the same or approximately the same to that of the adjunct material 106 such the entire surface of the adjunct material 106 is disposed on the polymer material 107. The polymer layer may also serve as a reservoir for medicants such as antimicrobials, chemotherapeutic agents, etc. or be radiopaque for imaging purposes.

As shown in FIG. 7, the polymer attachment layer 107 includes distal and proximal projections 117d, 117p facing the cartridge 102. FIG. 7 also illustrates that the distal and proximal projections 117d, 117p are formed on the polymer material 107 at locations corresponding to the locations of the adjunct's projections 116d, 116p, respectively. Thus, the distal projections 117d can be spaced from the proximal projections 117p along a longitudinal axis A1 of the polymer attachment layer 107 by the same distance by which the distal projections 116d are spaced from the proximal projections 116p. The projections 117d, 117p can be configured similarly to the adjunct's projections 116d, 116p—for example, the projections 117d, 117p can each optionally have an open-end channel extending least partially therethrough (not shown).

Also, the distal and proximal projections 117d, 117p of the polymer attachment layer 107 can have a length or diameter, as measured along the longitudinal axis A1, that is similar to that of a length or diameter of the distal and proximal projections 116d, 116p of the adjunct material 106. In some embodiments, the polymer attachment layer 107 can have a thickness from about 0.0005 inches to about 0.001 inches. The projections 117d, 117p can have a height or thickness from about 0.005 to about 0.010 inches. In some embodiments, the projections, which can be formed from an elastomeric material, can have a height in a range from about 0.005 inches to about 0.015 inches, in a range from about 0.003 inches to about 0.006 inches, or a height that varies in other ranges. However, in some embodiments, the projections 116d, 116p can have a height or thickness up to about 0.180 inches or greater.

The polymer attachment layer 107 can be formed from any suitable material such as, for example, polydioxanone (PDO), PLA/PGA copolymers, or any other suitable polymeric material(s), including pressure sensitive adhesive(s). Thus, the adjunct material 106 can be releasably engaged with the cartridge 102 via the polymer attachment layer 107. The polymer layer's projections 117d, 117p can be formed from the same material as the rest of the polymer attachment layer 107. Also, in some embodiments, the distal and proximal projections 117d, 117p can be formed from a different material than the material forming the polymer attachment layer 107. Because the material forming the polymer attachment layer 107 is biodegradable and/or bioabsorbable, the polymer attachment layer 107 can be implanted to a treatment site together with the adjunct 106. It should be appreciated that, in some embodiments, the polymer attachment layer 107 may not be present.

As mentioned above, the end effector 100 can be removably coupled with the loading member 105 having distal and proximal projections 115d, 115p and configured to apply force to the adjunct material 106 to thereby cause the adjunct material 106 to mate with the end effector 100. In particular, the application of force by the loading member 105 (and thus by the distal and proximal projections 115d, 115p thereof) to the adjunct material 106 causes the adjunct material's projections 116d, 116p to be at least partially received in the recesses 112d, 112p of the cartridge 102. Also, in embodiments such as in the example illustrated in which the polymer attachment layer 107 is disposed between the adjunct material 106 and the tissue-facing surface 110 of the cartridge 102, the application of force by the loading member 105 to the adjunct material 106 and thus to the polymer attachment layer 107 causes the polymer layer's projections 117d, 117p to be at least partially received in the recesses 112d, 112p of the cartridge 102. Furthermore, the adjunct material's projections 116d, 116p can be caused to be at least partially received within the polymer layer's projections 117d, 117p, respectively, as discussed below.

The distal and proximal projections 115d, 115p of the loading member 105, each of which can be in the form of two respective projections, can be configured in a number of different ways. For example, the distal and proximal projections 115d, 115p can have a length (measured along a longitudinal axis A2 of the loading member 105) that is similar to that of the adjunct material's projections 116d, 116p and the polymer layer's projections 117d, 117p. The distal and proximal projections 115d, 115p can have an open-end channel extending least partially therethrough and opening on a side of the loading member 105 facing the anvil 104, as shown in FIG. 6. However, in some implementations, one or more of the projections 115d, 115p may not include such channel.

Also, the distal and proximal projections 115d, 115p of the loading member 105 can be spaced apart from one another along the longitudinal axis A2 by approximately the same distance as the adjunct material's projections 116d, 116p and the polymer layer's projections 117d, 117p. In some embodiments, however, the distal and proximal projections 115d, 115p of the loading member 105 can be configured and/or formed on the loading member 105 in a different way. Furthermore, in some implementations, the loading member 105 may not include the distal and proximal projections 115d, 115p, or the loading member 105 may include only one projection, or other number (e.g., more than two) projections of any suitable configurations.

The loading member 105 can have a variety of different configurations. For example, the loading member 105 can be in the form of an applicator or retainer that can be removably coupled to the end effector 100. For example, in the illustrated implementation, as shown in FIGS. 6 and 7, the member 105 is an elongate, generally rectangular component having a length and width generally corresponding to the length and width of the tissue-contacting surface of the cartridge 102. The member 105 also has a distal tongue portion 120 in the form of a downward bent and a generally flat portion extending distally from the bend. The distal tongue portion 120 can facilitate grip and can serve as a lever. In use, the surgeon can hold the distal tongue portion 120 and apply force thereto in the direction towards the tissue-facing surface 110 of the cartridge 102 to thereby cause the member 105 to apply load to the adjunct material 106. The distal tongue portion 120 can be grasped and moved (e.g., moved away from the cartridge body 102) to remove the loading member 105 from the end effector 100.

Additionally or alternatively, the loading member 105 can be "preloaded," or releasably coupled with, the adjunct material 106 and the polymer attachment layer 107 in a suitable manner. When force is applied to the adjunct material 106, either by operating the loading member 105, or when the loading member 105 is clamped between the cartridge and anvil 102, 104, the adjunct material 106, and the polymer attachment layer 107 (if present) are transferred to the cartridge 102. The loading member 105 can then be removed from the end effector 100.

The loading member 105 can be coupled to the end effector 100 in many different ways. In the illustrated example, the loading member 105 is coupled to the proximal end 102p of the cartridge 102 using one or more suitable features. For example, the loading member 105 can have at a proximal end 105p thereof a tab 118 (FIG. 7) configured to engage the proximal end 102p of the cartridge body 102. It should be appreciated, however, that any other suitable feature(s) can be used to removably couple the member 105 to the cartridge body 102. Furthermore, in some implementations, the loading member 105 may not be coupled to the end effector 100—e.g., as discussed above it can be clamped between the end effector's jaws to thereby cause the adjunct material 106 (and the polymer attachment layer 107, if present) to be transferred to the cartridge 102.

In some embodiments, the adjunct material 106 and the polymer attachment layer 107 can be coupled to the loading member 105 in a suitable manner before the adjunct material 106 and the polymer attachment layer 107 are delivered to the cartridge body 102. Regardless of its configuration and the way in which it is used to cause the adjunct material to be releasably retained on a jaw of an end effector (e.g., the cartridge 102), the loading member 105 is configured to evenly apply force to the surface of the adjunct material 106 such that the adjunct material 106 becomes attached to the jaw.

Figure 8A:
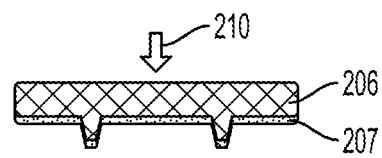
FIG. 8A is a cross-sectional view of a portion of the adjunct material and a polymer layer material of FIG. 7.
Figure 8B:
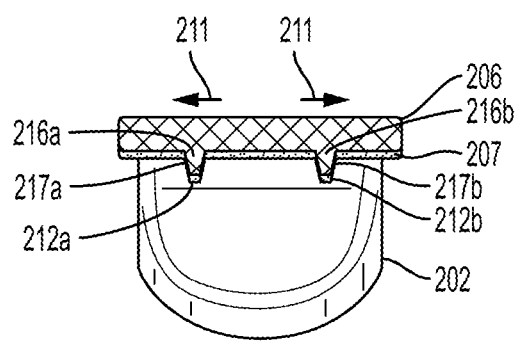
FIG. 8B is a cross-sectional view of a portion of the end effector of FIG. 7 having the adjunct material with the polymer layer material releasably retained thereon.

In some embodiments, as mentioned above, projections of the adjunct material can be at least partially received within the projections the polymer layer. FIGS. 8A and 8B demonstrate such an example where first and second projections 216a, 216b of an adjunct material 206 are at least partially received within first and second projections 217a, 217b of a polymer layer 207. The adjunct material 206 and the polymer layer 207 can be similar, for example, to the adjunct material and polymer layer 106, 107 (FIGS. 6 and 7), respectively. It should be appreciated that, while FIGS. 6 and 7 illustrate the adjunct material's and polymer layer's distal and proximal projections, FIGS. 8A and 8C show, by way of example, only respective pairs of distal projections formed on the adjunct material 206 and the polymer layer 207. Thus, for example, the first and second projections 216a, 216b of the adjunct material 206 can be similar to the at least one distal projection 116d of the adjunct material 106 in FIG. 7. It should be appreciated that the adjunct material 206 and the polymer layer 207 can also have respective proximal projections, similar, for example, to the at least one proximal projection 116p and at least one proximal projection 117p (FIG. 7), respectively.

As shown in FIG. 8A, the first and second projections 216a, 216b of the adjunct material 206 extend from the top into the first and second projections 217a, 217b of the polymer layer 207. The adjunct material 206 and the polymer layer 207 can be mated in this way in a number of different ways. For example, the adjunct material 206 can be preloaded with the polymer layer 207. Alternatively, the projections of the adjunct material 206 can be mated with the projections of the polymer layer 207 using the loading member or other component(s) configured to apply force to the adjunct material.

Regardless of the way in which the adjunct material 206 is mated with the polymer layer 207 so as to result in the structure as shown in FIG. 8A, such adjunct material/polymer layer structure can be caused (e.g., using the loading member 105 or another suitable component) to be engaged with the jaw of an end effector. For example, FIG. 8B illustrates that force can be applied (shown by arrow 210) to the adjunct material 206 mated with the polymer layer 207 to cause the first and second projections 217a, 217b of polymer layer 207 (and thus the first and second projections 216a, 216b of the adjunct material 206 mated therewith) to be engaged with corresponding first and second recesses 212a, 212b formed in a jaw 202. The jaw 202 can be a cartridge body (e.g., cartridge body 102 in FIGS. 6 and 7). However, the jaw 202 can also be an anvil, as the described techniques can be used to releasably retain an adjunct material on an anvil of the end effector as well.

A distance between the first and second recesses 212a, 212b formed in the jaw 202 can be greater than a distance between the first and second projections 217a, 217b of polymer layer 207 (and thus between the first and second projections 216a, 216b of the adjunct material 206), prior to mating the polymer layer 207 and the adjunct material 206 with the jaw 202. As a result of the force applied to the adjunct material 206 mated with the polymer layer 207, a distance between the first and second projections 217a, 217b (and thus between the first and second projections 216a, 216b) can increase, as shown in FIG. 8A by arrows 211. In this way, as the force is applied to the adjunct material 216 and its thickness thus decreases, the projections of the polymer layer 207 and of the adjunct material 206 "find" the first and second recesses 212a, 212b formed in the jaw 202 to thereby releasably mate the adjunct material 206 with the jaw 202.

Projections formed on an adjunct material in accordance with the described embodiments can have various configurations. For example, in some embodiments, the projections can be longitudinal projections formed on opposed sides of the adjunct material. The longitudinal projections formed on the adjunct material can be configured to be mated with complementary features (e.g., recesses) formed on a jaw of an end effector.

Figure 9:
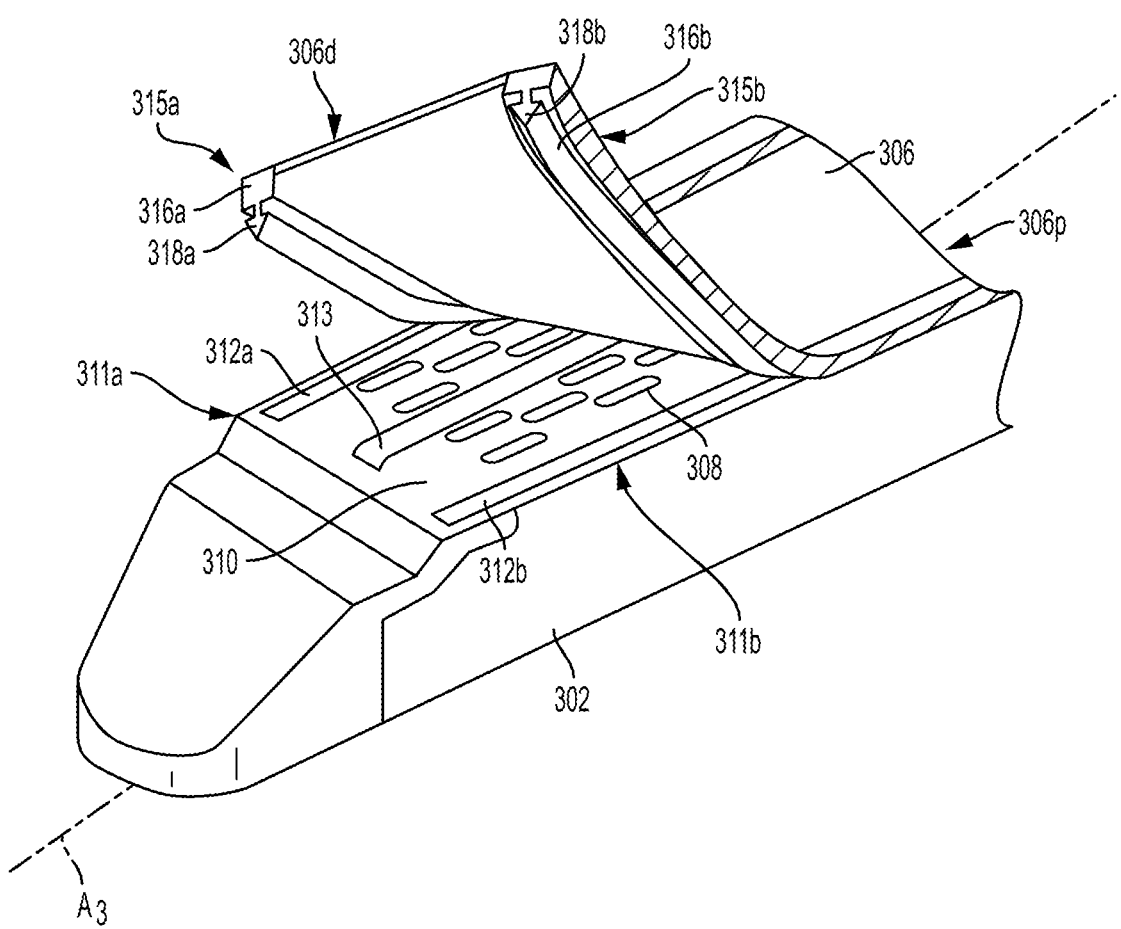
FIG. 9 is a perspective view of an end effector having an adjunct material releasably mounted thereon in accordance with the described techniques.
Figure 10:
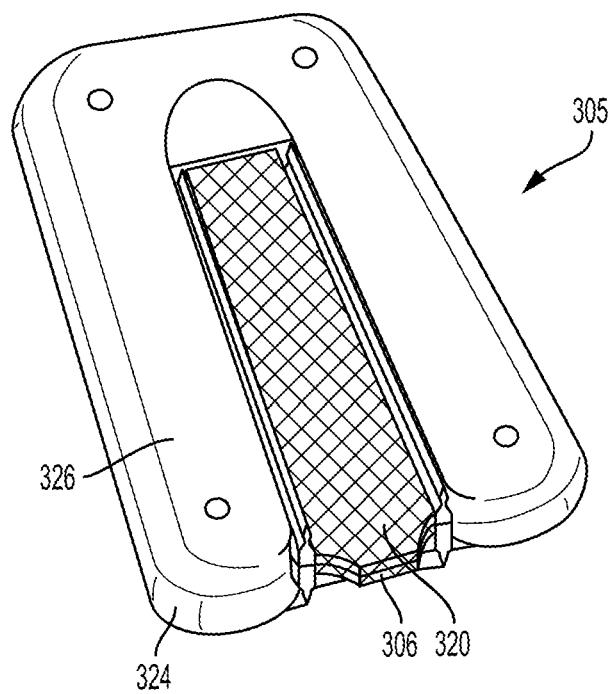
FIG. 10 is a perspective view of an applicator member configured to apply the adjunct material to the end effector of FIG. 9.
Figure 11:
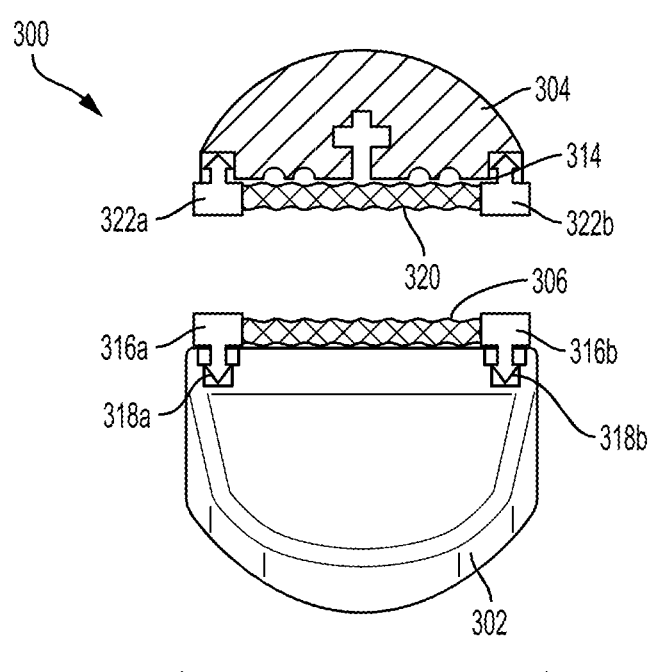
FIG. 11 is a cross-sectional view of a portion of the end effector of FIG. 9 having the adjunct material releasably retained thereon.

FIGS. 9-11 illustrate an embodiment of an end effector 300 having a cartridge 302 and an anvil 304, at least one of which can be configured to be releasably mated with an adjunct material having longitudinal projections. As shown in FIG. 9, the cartridge 302 has a plurality of staple cavities 308 configured to seat staples therein, the staple cavities formed on a tissue-facing surface 310 of the cartridge 302. The anvil 304 of the end effector 300, shown in FIG. 11, has a plurality of staple forming cavities (not shown) formed on a tissue-facing surface 314 thereof.

In the illustrated implementation, the end effector 300 can have an adjunct material releasably retained on one or both of the jaws 302, 304. Thus, as shown in FIG. 9, an adjunct material 306 can be releasably mated with the cartridge 302. The adjunct material 306 has a first longitudinal projection 316a formed on one side 315a of the adjunct material 306 and a second longitudinal projection 316b formed on another, opposite side 315b of the adjunct material 306. As shown, the first and second longitudinal projections 316a, 316b extend between distal and proximal ends 306d, 306p of the adjunct material 306.

The first and second longitudinal projections 316a, 316b of the adjunct material 306 are configured to mate with respective first and second complementary recesses 312a, 312b formed in the tissue-facing surface 310 of the cartridge 302. As shown in FIG. 9, the first and second longitudinal recesses 312a, 312b extend along a longitudinal axis A3 of the cartridge 302, are formed on opposed sides of a cutting element channel 313, and are each adjacent to opposed sides 311a, 311b of the tissue-facing surface 310.

The longitudinal projections 316a, 316b formed on the adjunct material 306 can have a number of different configurations. For example, the first and second longitudinal projections 316a, 316b of the adjunct material 306 have mating features 318a, 318b formed thereon that are configured to be at received within the corresponding recesses 312a, 312b. In this example, the mating features 318a, 318b are in the form of arrows facing towards the recesses 312a, 312b formed in the cartridge 302.

The longitudinal projections 316a, 316b can be formed from at least partially flexible and/or deformable material such that, as the projections 316a, 316b are received within the corresponding recesses 312a, 312b, the projections 316a, 316b contract to fit into the recesses and, once in the recesses, expand to be fittingly received within the recesses. Thus, the arrow-shaped mating features 318a, 318b extending from the adjunct material's longitudinal projections 316a, 316b can have a width that is greater than that of the respective recesses 312a, 312b. When the mating features 318a, 318b are forced into the recesses 312a, 312b, they can first be caused to contract as they are forced into the recesses, where they then expand to be releasably retained therein. It should be appreciated that the arrow-shaped mating features 318a, 318b are shown by way of example only, and the mating features formed on the projections can have any suitable configuration. For example, the mating features can be C-shaped, J-shaped, or they can have any other configuration(s), including different configurations.

As shown in FIG. 11, an adjunct material 320 configured to be releasably retained on the anvil 304 can have first and second longitudinal projections 322a, 322b, which can be similar to the longitudinal projections 316a, 316b formed on the adjunct material 306 configured to be releasably retained on the cartridge 302. For example, similar to the cartridge 302, the anvil 304 can have longitudinal recesses formed therein that are configured to receive therein the longitudinal projections 322a, 322b.

One or both of the adjunct materials 306, 320 can be releasably retained on the jaws 302, 304, respectively, using an applicator member 305 shown in FIG. 10. The applicator member 305 can be in the form of a frame-like holder configured to releasably retain one or both of the adjunct materials 306, 320. In the illustrated example, the applicator member 305 is in the form of first (e.g., bottom) and second (e.g., top) generally rectangular housings 324, 326 coupled to one another as shown in FIG. 10. As also shown in FIG. 10, the first and second housing 324, 326 can encompass edges of the long sides of the adjunct materials 306, 320 disposed within the applicator member 305. In other words, the applicator member 305 can be in the shape of a generally rectangular frame following an outer perimeter of at least two sides (e.g., long sides) of one or two adjunct materials. In particular, as shown in FIG. 10, the applicator member 305 encompasses at least in part the portions of the adjunct materials 306, 320 having first and second longitudinal projections 316a, 316b, and 322a, 322b, respectively, extending therefrom. The rest of the surface area of the adjunct materials 306, 320 may be not encompassed by the applicator member 305, as shown in FIG. 10. The adjunct material 320 to be retained on the anvil is disposed over the adjunct material 306 to be retained on the cartridge. It should be appreciated that the adjunct materials 306, 320 and the first and second housings 324, 326 of the applicator member 305 encompassing them can be symmetrical. Thus, either of the adjunct materials 306, 320 can be applied to the anvil or the cartridge.

The applicator member 305 can be formed from any suitable material (e.g., plastic), and its walls can be relatively thin and it can be disposable. In use, to transfer the adjunct materials 306, 320 to the cartridge and anvil 302, 304, respectively, the cartridge and anvil 302, 304 can be clamped over the applicator member 305. In this way, force applied by the jaws 302, 304 causes the adjunct materials 306, 320 to separate from the applicator member 305 and to be engaged with the jaws 302, 304. In particular, in this example, as force is applied to the applicator member 305 by the jaws 302, 304 of the end effector 300, the longitudinal projections 316a, 316b formed in the adjunct material 306 mate with the recesses 312a, 312b in the cartridge 302, and, similarly, the longitudinal projections 322a, 322b formed in the adjunct material 320 mate with the complementary recesses (not shown) in the anvil 304.

After the adjunct materials 306, 320 are transferred to the cartridge and anvil 302, 304, the cartridge and anvil 302, 304 can be opened and the applicator member 305 can be separated from the end effector 300. The end effector 300 having its cartridge and anvil 302, 304 thus mated with the adjunct materials 306, 320, as shown in FIG. 11, can then be used as desired in a surgical procedure.

It should be appreciated that the applicator member 305 is shown to releasably retain both of the adjunct materials 306, 320 by way of example only, as the applicator member 305 or a similar component configured to releasably hold at least one adjunct material can be used to transfer an adjunct material only to an end effector's anvil or an end effector's cartridge.

In some embodiments, at least one projection formed on the adjunct material can be in the form of a plurality of discrete projections formed from an at least partially flowable or bendable material that has a changeable configuration. When a suitable applicator applies force to the adjunct material to cause each of the discrete projections to be at least partially received within a corresponding recess in a jaw of an end effector, the configuration of each of the discrete projections that is at least partially received within the corresponding recess changes to conform to a configuration of the corresponding recess. The discrete projections are configured to separate from the adjunct material and remain within the recesses in the jaw after the staples are formed against the staple forming cavities to apply the adjunct material to a tissue clamped between the end effector's jaws.

Figure 12:
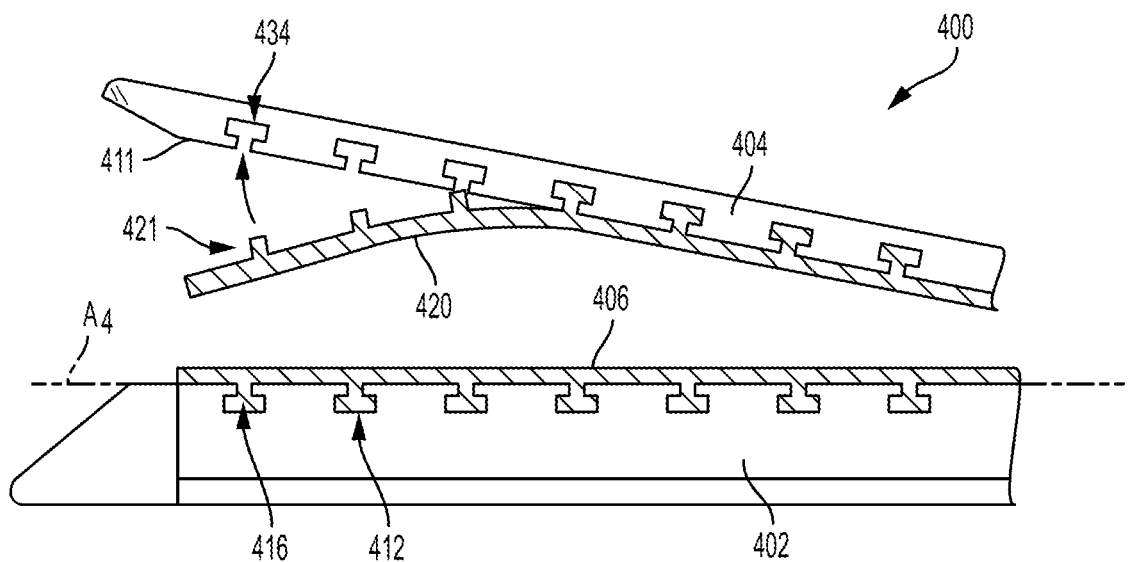
FIG. 12 is a perspective, partially exploded view of an end effector having first and second adjunct materials releasably mounted thereon in accordance with the described techniques.
Figure 13:
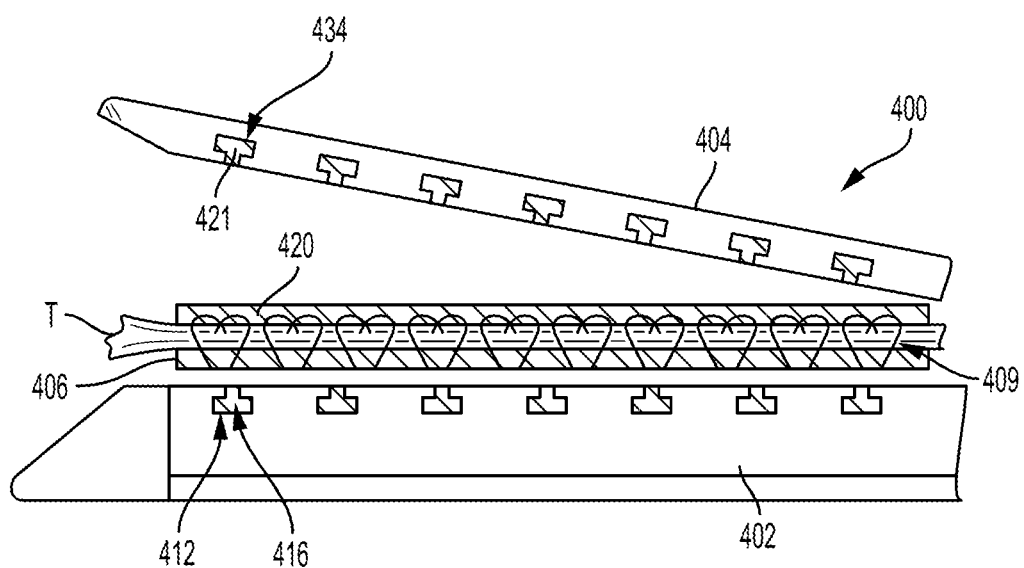
FIG. 13 is a perspective, partially exploded view of the end effector of FIG. 12, illustrating the first and second adjunct materials applied to a tissue in a patient.
Figure 14:
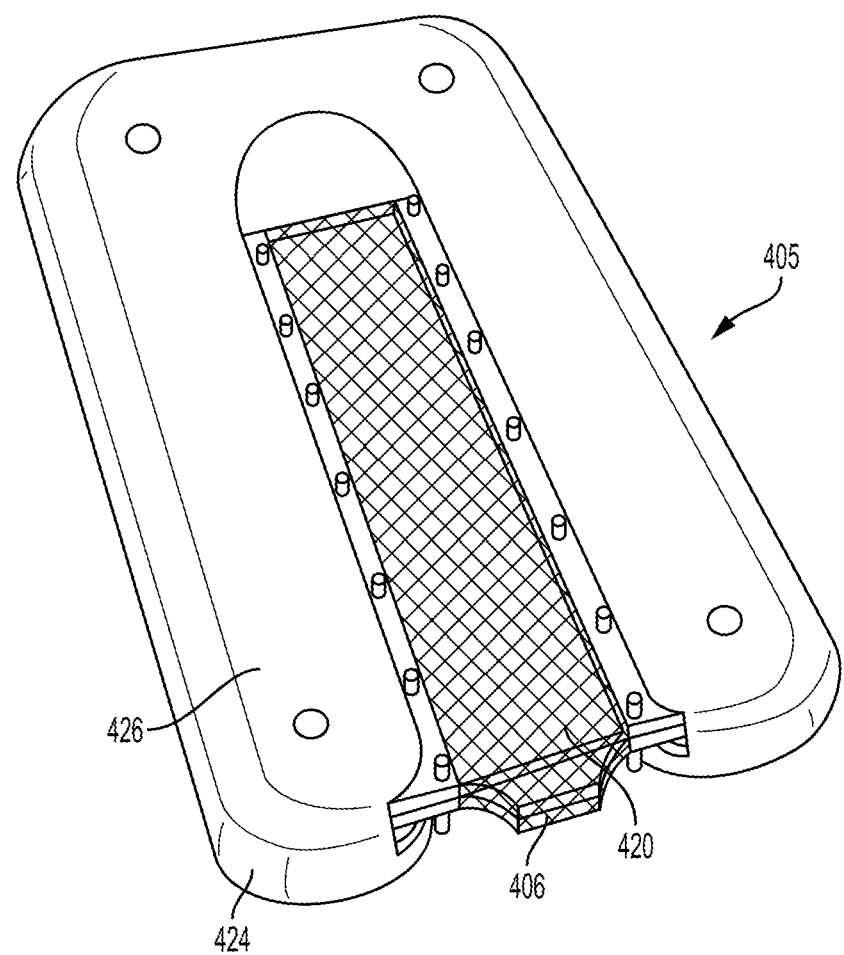
FIG. 14 is a perspective view of an applicator member configured to apply the first and second adjunct materials to the end effector of FIG. 12.

FIGS. 12-14 illustrate anther embodiment of an end effector 400 having a cartridge 402 and an anvil 404, at least one of which can have an adjunct material releasably retained thereon that is has projections made from an at least partially flowable material. The projections can also be formed from at least partially bendable, free-flowing, or waxy materials. In other words, the material from which the projections are formed can be deformable in various ways. For example, they can be made from polymers/elastomers may deform or bend and still retain memory of their original shape.

In this example, as shown in FIG. 12, both the cartridge 402 and the anvil 404 can have respective adjunct materials 406, 420 to be releasably retained thereon. As shown in FIG. 12, the adjunct material 406 releasably retained on a tissue-facing surface 410 of the cartridge 402 has a plurality of discrete projections 416 configured to be releasably mated with recesses 412 formed in the tissue-facing surface 510. As shown in FIG. 12, the discrete projections 416 are formed along a longitudinal axis A4 of the adjunct 406. It should be appreciated that the projections 416 and recesses 412 do not need to be evenly spaced and, in some embodiments, they can be disposed at varied distances from one another. The locations and number of the projections 416 and recesses 412 can be selected based on a desired manner of attaching the adjunct material to the end effector's jaw. Accordingly, the seven evenly spaced projections 416 are shown in FIG. 12 by way of example only, as suitable number of projections can be formed, and the projections can be formed asymmetrically and unevenly spaced with respect to one another.

The adjunct material 420 releasably retained on a tissue-facing surface 411 of the anvil 402 also has a plurality of discrete projections 421 configured to be releasably mated with recesses 434 formed in the tissue-facing surface 411. It should be appreciated that each of the discrete projections 416, 421 can be formed such that it spans the entirety of, or only a portion of, the width of the respective jaw. Also, in some implementations, each of the discrete projections 416, 421 can be in the form of two projections formed on opposed sides of the tissue-facing surface of the jaw, although only one of such projections is shown in FIG. 12.

In this example, the discrete projections 416 formed on the adjunct material 406 and the discrete projections 421 formed on the adjunct material 420 have a generally rectangular shape, as shown in FIG. 12 (where the projections of the anvil's adjunct material 420 are shown partially separated from the anvil 404). The discrete projections 416, 421 can be formed from an at least partially flowable material and can have a changeable configuration such that, when each of the discrete projections is at least partially received within a corresponding recess in the jaw, the configuration of each discrete projection changes to conform to a configuration of the corresponding recess. The at least partially flowable material can be any suitable material or a combination of materials. Examples of the materials can include a suitable polymeric material, elastomeric material (e.g., silicone), wax, and any other material(s). For example, collagen, gelatin hyaluronic acid, sodium alginate, or any other hydrogels can be used. Also, non-limiting examples of materials can include materials described in U.S. Pat. Pub. No. 2016/0278774 entitled "Method of Applying a Buttress to a Surgical Stapler," filed on Mar. 25, 2015, which is hereby incorporated by reference herein in its entirety.

In some embodiments, a more rigid polymer/elastomer can be used that can be perforated/slitted at the end, such that it frays outward into a T-slot pocket, rather than deforming in bulk, which would require a material with very low shear-resistance. In some embodiments, a material from which the adjunct is formed can be used to fill out the recess on its own. This may be possible with non-woven fabrics having fibers that are able to slide/shear relative to each other.

Accordingly, in the illustrated implementation, each of the generally rectangular projections 421 formed on the adjunct material 420 to be releasably retained on the anvil 404, "flows" into, or conforms, to the configuration of each of the recesses 434, as shown in FIG. 12. As also shown in FIG. 12, the projections 416 of the adjunct 406 (which can also be generally rectangular projections) "flow" into the T-shaped recesses 412 formed in the cartridge 402 to thus conform to the shape of the recesses 412.

The adjunct materials 406, 420 can be transferred to the cartridge and anvil 402, 404 using an applicator member 405 shown in FIG. 14, which can be similar to applicator member 305 (FIG. 10). Thus, as shown in FIG. 14, the applicator member 405 can be a frame-like holder having first and second portions 424, 426 releasably holding the adjunct materials 406, 420. To transfer the adjunct materials 406, 420 from the applicator member 405 to the end effector 400, the jaws 402, 404 can be clamped upon the applicator member 405, which causes the adjunct materials 406, 420 to be mated with the cartridge and anvil 402, 404, respectively. In particular, as discussed above, the projections, on the adjunct materials 406, 420 are received in the recesses 412, 434 in the cartridge and anvil 402, 404 so that the projections (which are formed from at least partially flowable material) change their configuration to fill in the recesses and thus adopt the shape of the recesses. Similar to the applicator member 305 (FIG. 10), after the applicator member 405 is used to transfer the adjunct materials 406, 420 to the end effector's jaws, the applicator member 405 can be separated from the end effector 400.

During a surgical procedure, as shown in FIG. 13, a tissue T is clamped between the cartridge 402 and anvil 404 of the end effector 400 and staples 409 are formed against the staple forming cavities of the anvil 404. The ejection of the staples from the staple-holding cavities opening on the tissue-facing surface 410 of the cartridge 402 causes the adjunct materials 406, 420 to be released from engagement with the cartridge 402 and anvil 404 and to be applied to opposed sides of the tissue T, as also shown in FIG. 13. As further shown in FIG. 13, the discrete projections 416, 421 separate from the adjunct materials 406, 420 applied to the tissue T and remain within the recesses 412, 434, respectively. Such embodiments can be employed in implementations where, for example, the end effector 400 is part of a disposable loading unit configured to be coupled distally to a surgical tool and that is configured to be disposed after use.

In some embodiments, an adjunct material configured to be releasably retained on a jaw of an end effector can be formed from at least partially expandable or stretchable material and/or in the form of a film. The jaw, such as an anvil or a cartridge, can have one or more recesses formed therein that are configured to receive portions of the adjunct material. An applicator member, such as, e.g., loading member 305 in FIG. 10, applicator member 405 in FIG. 14, or a member having any other configuration that has projections formed thereon, can be used to mate the adjunct material with the jaw. For example, when the applicator member is used to apply force to the adjunct material, the projections formed on the applicator member cause portions of the adjunct material to be releasably received within the one or more recesses formed in the jaw.

Figure 15:
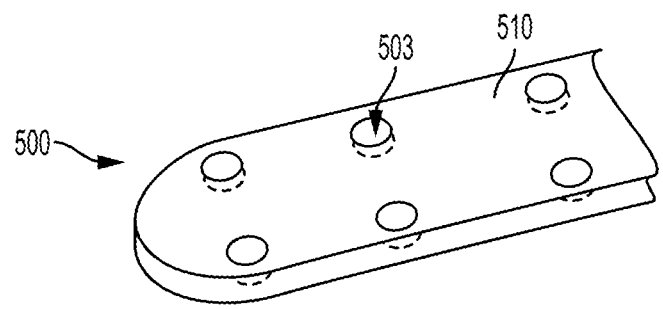
FIG. 15 is a perspective, schematic view of a jaw of an end effector having recesses formed thereon that are configured to mate with portions of an adjunct material in accordance with the described techniques.
Figure 16:
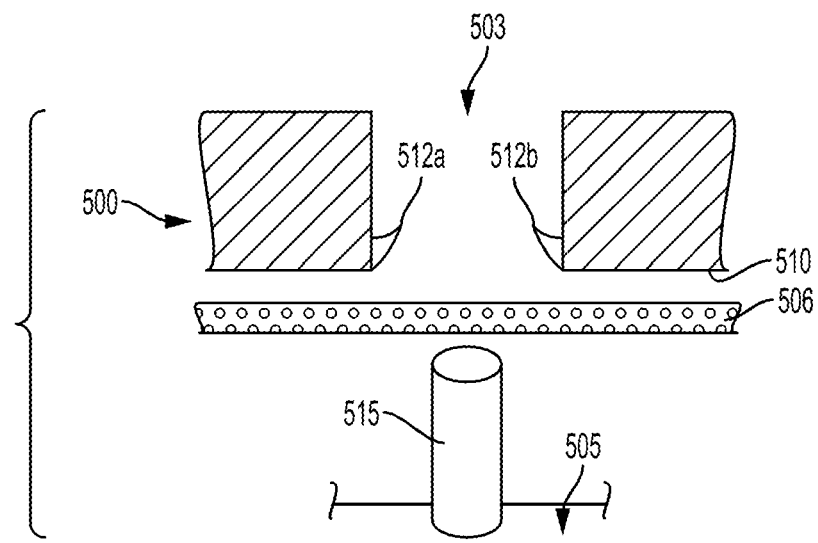
FIG. 16 is a perspective, schematic view of the jaw of FIG. 15 and of an applicator member configured to cause the portions of the adjunct material to be received in the recesses in the jaw.
Figure 17:
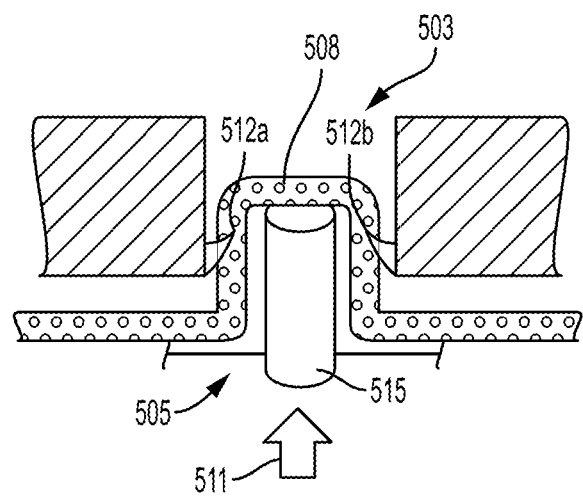
FIG. 17 is a perspective, schematic view of the jaw of FIG. 15, illustrating the portions of the adjunct material received in the recesses in the jaw using the applicator member.

FIGS. 15-17 illustrate one example of an implementation of an adjunct material 506 configured to be mated with a jaw 500 of an end effector of a surgical instrument. In this example, the jaw 500 is shown generally as a jaw that can be either a cartridge or an anvil. Regardless of its particular configuration, the jaw 500 can have recesses 503 formed in a tissue-facing surface 510 thereof. It should be appreciated that the recesses 503 can be formed at any locations within tissue-facing surface 510. Also, the six recesses 503 are shown in FIG. 15 for illustrating purposes only, as any suitable number of recesses 503 (e.g., less than six or greater than six) can be formed on the jaw. Also, the recesses 503 do not need to be evenly spaced and, in some embodiments, they can be disposed at varied distances from one another. The locations and number of the recesses 503 can be selected based on a desired manner of attaching the adjunct material to the end effector's jaw.

For example, the recesses 503 can be formed in the area of the tissue-facing surface 510 occupied by staple-forming cavities (if the jaw 500 is an anvil) or by staple-holding cavities or pockets (if the jaw 500 is a cartridge). As another example, one or more of the recesses 503 can be formed in area(s) of the tissue-facing surface 510 that does not have the staple-forming cavities or the staple-holding pockets. For example, in one embodiment, one or more recesses can be formed at a distal end of the jaw 500 outside of the area having the staple-forming cavities or the staple-holding pockets, and one or more recesses can be formed at a proximal end of the jaw 500 outside of the area having the staple-forming cavities or the staple-holding pockets. Furthermore, in some implementations, one or more of the recesses 503 can be the staple-forming cavities or the staple-holding pockets.

The recesses 503 are shown by way of example only as having a generally circular cross-section. However, the recesses 503 can have other suitable shapes, as the described embodiments are not limited in this respect. One or more of the recesses 503 can have features that facilitate their ability to retain a portion of the adjunct material therein. For example, as shown in FIG. 16, the recess 503 can have retaining features 512a, 512b that can be in the form of hooks, teeth, rings, barbs, or retaining elements having any other configuration. It should be appreciated that one or more of the retaining features can be formed, or the recesses 503 can be free of any additional features.

Regardless of the way in which the recesses 503 are formed in the jaw 500, each recess (e.g., the recess 503 shown in FIG. 16) is configured to receive therein a corresponding projection or post 515 formed on an applicator member 505. The applicator member 505, having one or more posts (one of which is shown in FIGS. 16 and 17), can have any suitable configuration that enables force to be applied by the applicator member 505 to the adjunct material 506. As mentioned above, the adjunct material 506 can be formed from an at least partially stretchable material. Thus, as shown in FIG. 17, when force is applied by or to the applicator member 505 (as shown by arrow 511), the applicator member 505 is brought in proximity to the tissue-facing surface 510 such that the post 515 is at least partially received within the recess 503. As a result, the post 515 pushes a portion 508 of the adjunct material 506 into the recess 503, as also shown in FIG. 17. In this example, the retaining features 512a, 512b extending from the inner walls of the recess 503 facilitate retention of the portion 508 of the adjunct material 506 within the recess 503.

Other recesses formed in the jaw 500 can similarly receive at least partially therein posts formed on the applicator member 505 that thus push portions of the adjunct material 506 into the recesses. In this way, the adjunct material 506 becomes releasably mated with the jaw 500.

The number and locations of the posts, such as the post 515, formed on the applicator member 505 can correspond to those of the recesses 503 in the jaw 500. Thus, each of the recesses 503 can receive therein a portion of the adjunct material pushed into the recess using a corresponding post. In other implementations, however, only some of the recesses can receive corresponding posts therein.

The post 515, representing just one example of the multiple posts that can extend from the applicator member 505, is shown as a generally cylindrical element by way of example only, as the post 515 can have other configurations. For example, the post 515 can be mushroom-shaped (e.g., shaped as a "reversed mushroom") or it can have a generally rectangular, square, or otherwise shaped cross-section. The size of the post 515 can be selected such that it fits with clearance within the recess 503 and pushes the portion 508 of the adjunct material 506 into the recess 503 in a manner that allows retaining that portion 508 in the recess 503, as shown in FIG. 17. The portion 508 can be retained in the recess 503 using the retaining features 512a, 512b as shown in FIGS. 16 and 17, or any other type(s) of retaining features.

After the adjunct material 506 is mated with the jaw 500 using the applicator member 505, the applicator member 505 is removed, whereas the adjunct material portion 508 remains in the recess 503. When the adjunct material 506 is separated from the jaw 500 to be transferred to a tissue at a treatment site (e.g., when staples are ejected from the jaw's cartridge), the adjunct material portion 508 is caused to exit the recess 503.

In the illustrated example, the adjunct material 506, which can be in the form or a film and/or at least partially stretchable member, can be generally rectangular or it can have other configurations. The size of the adjunct material 506 can be such that, when its portions (e.g., the portion 508 in FIGS. 16 and 17) are mated with the jaw 500, the adjunct material 506 still covers a desired area of the tissue-facing surface 510 of the jaw 500. In other words, the adjunct material 506 can be oversized relative to a size of the tissue-facing surface 510 of the jaw 500. Also, even though some extra material becomes available after the adjunct material's portions are released from the recesses in the jaw, this does not affect the ability of the adjunct material 506 to reinforce and/or treat a site in a patient's body.

Figure 18:
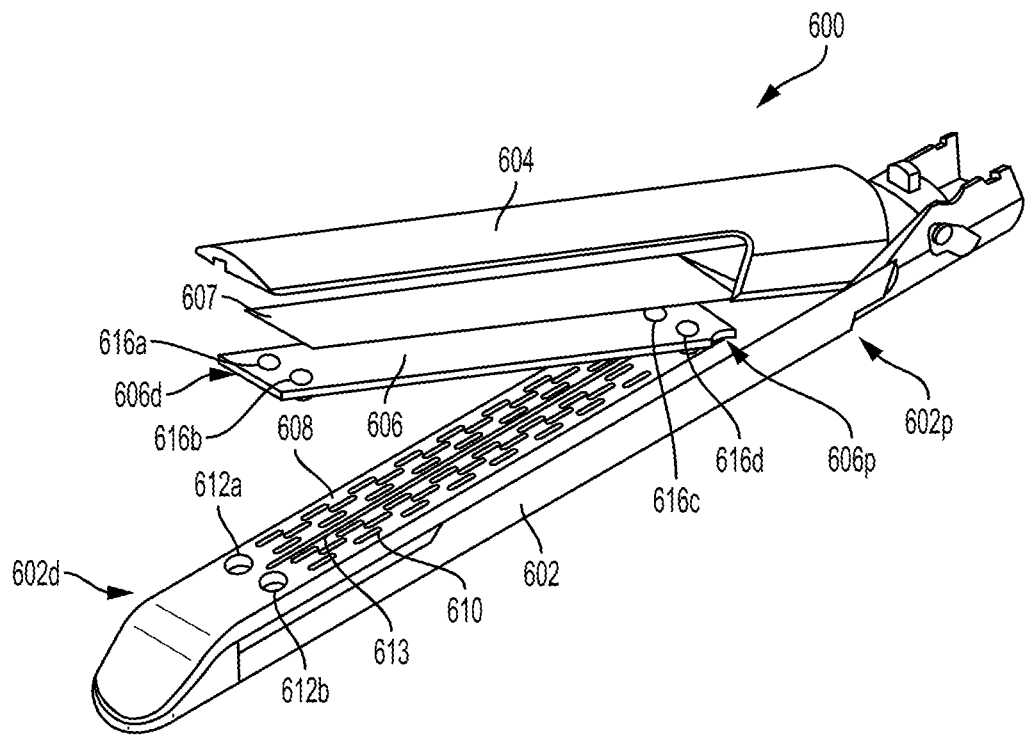
FIG. 18 is a perspective view of an end effector having an adjunct material releasably mounted thereon in accordance with the described techniques.
Figure 19:
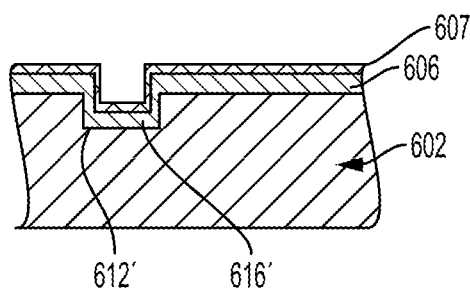
FIG. 19 is a cross-sectional view of a portion of the end effector of FIG. 18 having the adjunct material releasably retained thereon.

In some embodiments, an adjunct material can be releasably retained on a jaw of an end effector using a material that can change its configuration when heat is applied thereto. FIGS. 18 and 19 illustrate an embodiment of an end effector 600 having a cartridge body 602 and an anvil 604, which can have an adjunct material 606 configured to be retained on at least one of the cartridge body and anvil 602, 604 using an attachment layer 607. In particular, in the example illustrated, the attachment layer 607 can be used to couple the adjunct material 606 to the cartridge body 602, as discussed in more detail below.

As shown in FIG. 18, a tissue-facing surface 610 of the cartridge body 602 can have recesses 612a, 612b disposed outside of the area of the cartridge body 602 having staple-holding pockets 608. The two recesses 612a, 612b formed at a distal end 602d of the cartridge body 602 are shown, and a proximal end 602p of the cartridge body 602 can have a similar pair of recesses. The recesses 612a, 612b are disposed at opposed sides of a cutting-element channel 613 in the cartridge body 602, though the recesses 612a, 612b can be disposed at other areas of the tissue-facing surface 610 of the cartridge body 602.

As shown in FIG. 18, the adjunct material 606 can have retaining features 616a, 616b formed at a distal end 606d thereof, and similar retaining features 616c, 616d formed at a proximal end 606p thereof. In the illustrated implementation, the retaining features 616a, 616b, 616c, 616d are in the form of cupcake-like depressions in the adjunct material 606 extending towards the cartridge body 602 and opening on a side of the adjunct material 606 opposite to its side facing the cartridge body 602. It should be appreciated, however, that the retaining features 616a, 616b, 616c, 616d can have any other shapes, and that the number of the retaining features can be different from four (e.g., less than four or greater than four). Furthermore, as in the example illustrated, the retaining features 616a, 616b, 616c, 616d can be formed as closed depressions in the adjunct material 606, or they can be open-ended features opening into the cartridge's recesses when the adjunct is mated therewith.

The distal retaining features 616a, 616b are configured to be received within the distal recesses 612a, 612b in the cartridge body 602. In a similar manner, the proximal retaining features 616c, 616d of the adjunct material 606 are configured to be received within the proximal recesses formed in the cartridge body 602, which are obscured in FIG. 18.

The attachment layer 607, which can be formed from a suitable heat meltable material, can be used to attach the adjunct material 606 to the cartridge body 602. For example, to releasably attach the adjunct material 606 to the cartridge body 602, the adjunct material 606, which can have the attachment layer 607 coupled thereto in a suitable manner, can be disposed on the tissue-facing surface 610 of the cartridge body 602. The attachment layer 607 can be coupled to the adjunct material 606 or it can be disposed over the adjunct material 606 such that the adjunct material 606 is located between the tissue-facing surface 610 of the cartridge body 602 and the attachment layer 607. Regardless of the way in which the attachment layer 607 is associated with the adjunct material 606, the adjunct material 606 is disposed over the cartridge body 602 such that the retaining features 616a, 616b, 616c, 616d are received within the respective recesses formed in the cartridge body 602. For example, the retaining features 616a, 616b are received within the recesses 612a, 612b.

A suitable device can then be used to apply heat to the attachment layer 607 such that at least some of its portions melt and the attachment layer's material flows into the retaining features 616a, 616b, 616c, 616d in the adjunct material 606 that, in turn, at least partially seat within respective recesses formed in the cartridge body 602. In this way, the material of the attachment layer 607 deposited within each of the retaining features 616a, 616b, 616c, 616d of the adjunct material 606 mates the adjunct material 606 with the cartridge body 602. FIG. 19 illustrates by way of example a recess 612' in the cartridge body 602, which can be representative of any of the recesses (e.g., 612a, 612b or others) that can be formed in the cartridge body 602. As shown in FIG. 19, the recess 612' can seat therein a respective retaining feature 616' (e.g., any of the retaining features 616a, 616b, 616c, 616d) that in turn, is lined with the material of the attachment layer 607.

The attachment layer 607 can be formed from any suitable bioabsorbable and/or biodegradable material. Non-limiting examples of the material include polydioxanone (PDO), lactide/glycolide copolymers, poly-L-lactide, poly-L-lactide-co-D,L-lactide, poly-L-lactide-co-glycolide, poly-4-hydroxybutrate, polycaprolactone, poly lactide-co-glycolide), Poly-L-lactide. Exemplary materials are also disclosed in U.S. patent application Ser. No. 14/871,195, entitled "Compressible Adjunct Assemblies with Attachment Layers" and Ser. No. 14/871,087, entitled "Implantable Adjunct Comprising Bonded Layers."

Heat of a suitable temperature such as, for example, between 80° C.° and 120° C.°, can be applied to the end effector 600 in any of various ways. Though, other ranges can be used as well, including higher temperatures. For example, a suitable heater device (e.g., an infrared (IR) heater, ultraviolet (UV) heater, resistive heater, etc.) can be used.

In some implementations, the adjunct material 606 and the attachment layer 607 can be coupled to the jaw of the end effector 600, such as the cartridge body 602, using an applicator member (not shown) configured to apply the adjunct material 606 with the attachment layer 607 to an end effector's jaw. The applicator member can be similar, e.g., to the applicator member 305 (FIG. 10), but can also be equipped with a heating element (e.g., a resistive wire element, UV element, IR element, etc.). Similar to the applicator member 305, the heat-applying applicator member can releasably hold the adjunct material 606 and the attachment layer 607. Regardless of the specific way in which the applicator member is configured to generate heat, in use, the applicator member can be clamped between the jaws 602, 604 of the end effector 600 and activated to generate heat to thus melt at least portions of the attachment layer 607. After the attachment layer 607 is received within the retaining features of the adjunct material 606 (e.g., as shown in FIG. 19), the jaws 602, 604 can be open and the applicator member can be separated from the end effector 600 while leaving the adjunct material 606 and the attachment layer 607 mated with the end effector 600 (in this example, with the cartridge body 602).

It should be appreciated that, additionally or alternatively, an adjunct material can be configured to be releasably mated with an anvil in a manner similar to that shown in FIGS. 18 and 19.

In the embodiments described herein, an adjunct material for use with an end effector of a surgical instrument is provided that has at least one projection configured to mate with a corresponding at least one recess formed in the end effector. However, in other embodiments, an adjunct material can be releasably retained on a jaw of an end effector using recesses formed in the adjunct material that are configured to mate with corresponding projections formed on the jaw.

Figure 20:
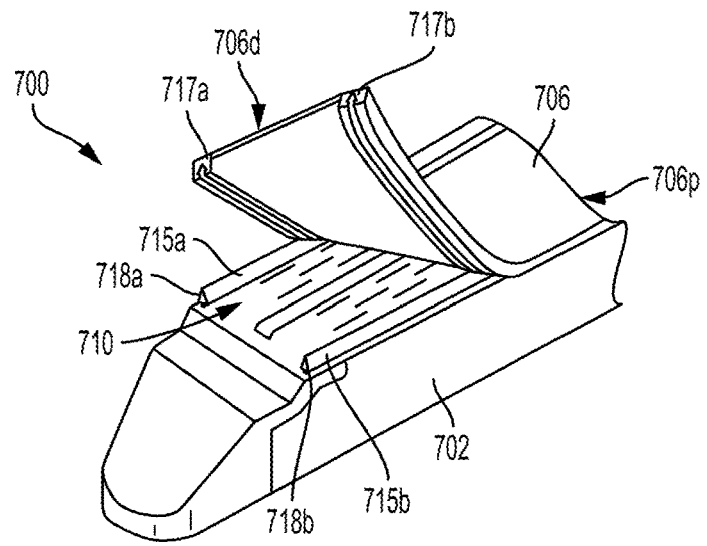
FIG. 20 is a perspective view of an end effector having an adjunct material releasably mounted thereon in accordance with the described techniques.
Figure 21:
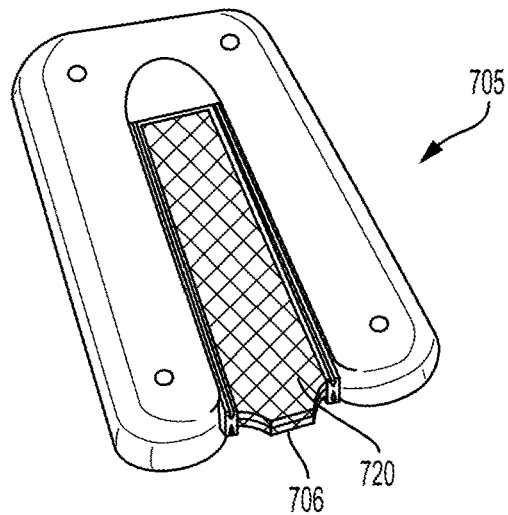
FIG. 21 is a perspective view of an applicator member configured to apply the adjunct material to the end effector of FIG. 20.
Figure 22:
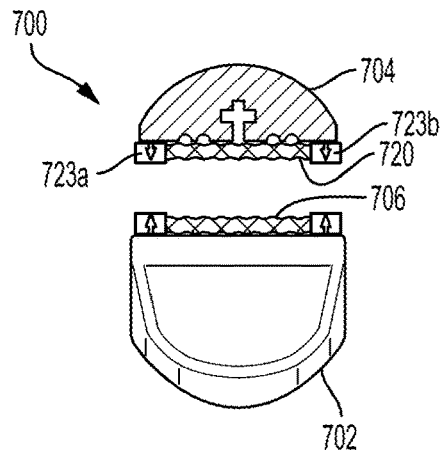
FIG. 22 is a cross-sectional view of a portion of the end effector of FIG. 20 having the adjunct material releasably retained thereon.

FIGS. 20-22 illustrate an embodiment of an end effector 700 having a cartridge 702 and an anvil 704, at least one of which can be configured to be releasably mated with an adjunct material having longitudinal channels or recesses. In this embodiment, the end effector 700 has a cartridge 702 and an anvil 704 having any suitable configurations, at least one of which can be configured to be releasably mated with an adjunct material having longitudinal recesses. For example, as shown, the end effector 700 can have adjunct materials releasably retained on both of the jaws 702, 704. Thus, as shown in FIG. 20, an adjunct material 706 can be releasably mated with the cartridge 702. The adjunct material 706 has a first longitudinal recess 717a formed on one side of the adjunct material 706 and a second longitudinal recess 717b formed on another, opposite side of the adjunct material 706. As shown, the first and second longitudinal recesses 717a, 717 extend between distal and proximal ends 706d, 706p of the adjunct material 706.

The first and second longitudinal recesses 717a, 717b of the adjunct material 706 are configured to mate with respective first and second complementary projections 715a, 715b formed on a tissue-facing surface 710 of the cartridge 702. The projections 715a, 715b can have mating features 718a, 718b formed thereon that are configured to mate with the corresponding recesses 717a, 717b in the adjunct material 706. In this example, the mating features 718a, 718b are in the form of arrows facing towards the adjunct material 706, as shown in FIGS. 20-22. It should be appreciated that the arrow-shaped mating features 318a, 318b are shown by way of example only, and the mating features formed on the projections can have any suitable configuration. For example, the mating features can be C-shaped, J-shaped, or they can have any other configuration(s), including different configurations.

The longitudinal recesses 717a, 717b formed in the adjunct material 706 can have a number of different configurations. For example, the first and second longitudinal recesses 717a, 717b can have a shape that is complementary to that of the first and second projections 715a, 715b. In this way, as in the example illustrated, at least a portion of each of the first and second longitudinal recesses 717a, 717b can be arrow-shaped. However, the recesses 717a, 717b can have any other suitable configuration(s).

The longitudinal projections 715a, 715b can be formed from at least partially flexible and/or deformable material such that, as the projections 715a, 715b are received within the corresponding recesses 717a, 717b in the adjunct material 706, the projections 715a, 715b are contracted to fit into the recesses and, once in the recesses, are then expanded to be fittingly received within the recesses.

As shown in FIG. 22, an adjunct material 720 configured to be releasably retained on the anvil 704 can also have first and second longitudinal recesses 723a, 723b, which can similar to the longitudinal recesses 717a, 717b formed on the adjunct material 706 configured to be releasably retained on the cartridge 702. For example, similar to the cartridge 702, the anvil 704 can have longitudinal projections formed therein that are configured to be received within the longitudinal recesses 723a, 723b. Similar to the example shown in FIGS. 9-11, one or both of the adjunct materials 706, 720 can be releasably retained on the jaws 702, 704, respectively, using an applicator member 705 shown in FIG. 21. The applicator member 705, which can releasably retain therein the adjunct materials 706, 720, can be similar to the applicator member 305 (FIG. 10) and is therefore not described in detail herein.

It should be appreciated that the adjunct materials described herein can include one or more medicants which can be releasably incorporated into or associated with adjuncts in many different ways. Also, the adjunct materials can have various other features in addition to the features described herein.

A person skilled in the art will appreciate that the subject matter described herein has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the described subject matter disclosure based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. An end effector for a surgical instrument, comprising:
a first jaw having a cartridge, the cartridge including:
a plurality of staple cavities configured to seat staples therein, the staple cavities opening on a tissue-facing surface of the cartridge, and
a cutting element channel extending between proximal and distal ends of the cartridge, and
at least one recess opening on the tissue-facing surface of the cartridge;
a second jaw opposing the first jaw and having an anvil with a plurality of staple forming cavities formed on a tissue-facing surface thereof, wherein the first and second jaws are configured to clamp tissue therebetween;

an adjunct material having at least one projection configured to mate with the at least one recess of the cartridge to retain the adjunct material on the first jaw; and a removable applicator member configured to apply force to the adjunct material to cause the at least one projection of the adjunct material to be at least partially received in a corresponding recess of the at least one recess formed in the cartridge to thereby cause the adjunct material to be releasably mated with the first jaw, wherein the removable applicator member includes at least one applicator member projection facing the adjunct material and formed on the applicator member at a location thereof corresponding to a location of the at least one projection of the adjunct material.

2. The end effector of claim 1, wherein the at least one recess comprises, two or more recesses formed at a distal end of the cartridge and formed on opposite sides on the cutting element channel, and two or more recesses formed at a proximal end of the cartridge and formed on opposite sides of the cutting element channel.

3. The end effector of claim 1, wherein the removable applicator member is configured to releasably hold the adjunct material so as to release the adjunct material when the removable applicator member is clamped between the first and second jaws.

4. The end effector of claim 1, wherein, when the removable applicator member is configured to apply the force to the adjunct material, the at least one applicator member projection is configured to cause the at least one projection of the adjunct material to be at least partially received in the corresponding recess.

5. The end effector of claim 1, further comprising a polymer attachment layer configured to be positioned between the first jaw and the adjunct material.

6. The end effector of claim 5, wherein the polymer attachment layer includes at least one second projection facing the adjunct material and formed on the polymer attachment layer at a location thereof corresponding to a location of the at least one projection of the adjunct material.

7. The end effector of claim 6, wherein, when the removable applicator member is configured to apply the force to the adjunct material and to the polymer attachment layer positioned between the first jaw and the adjunct material, the at least one applicator member projection is configured to cause the at least one projection of the adjunct material and the at least one second projection of the polymer attachment layer to be at least partially received in the corresponding recess.

8. The end effector of claim 1, wherein the at least one projection includes at least one longitudinal projection that extends between distal and proximal ends of the adjunct material.

9. The end effector of claim 8, wherein the at least one longitudinal projection has a mating feature formed thereon that is configured to be received within the corresponding recess, and wherein the at least one longitudinal projection is formed from at least partially flexible material such that, as the at least one longitudinal projection is received within the corresponding recess, the longitudinal projection is contracted due to the force being applied by the removable applicator member and then expanded to be fittingly received within the corresponding recess.

10. The end effector of claim 1, wherein the at least one projection comprises a plurality of discrete projections formed from an at least partially flowable material and having a changeable configuration such that, when the removable applicator member applies the force to the adjunct material to cause each of the discrete projections to be at least partially received within its corresponding recess, the configuration of each discrete projection that is at least partially received within its corresponding recess changes to conform to a configuration of its corresponding recess.

11. The end effector of claim 10, wherein each of the discrete projections is configured to separate from the adjunct material and remain within its corresponding recess after the staples are formed against the staple forming cavities to apply the adjunct material to a tissue clamped between the first and second jaws.

12. An end effector for a surgical instrument, comprising:

a first jaw having a cartridge with at least one recess formed therein and a plurality of staple cavities configured to seat staples therein, the at least one recess and the staple cavities each opening on a tissue-facing surface of the cartridge;

a second jaw opposing the first jaw and having an anvil with a plurality of staple forming cavities formed on a tissue-facing surface thereof, wherein the first and second jaws are configured to clamp tissue therebetween;

an adjunct material having at least one projection configured to mate with the at least one recess to retain the adjunct material on the first jaw; and a removable applicator member configured to apply a load to the adjunct material when manual force is applied to the removable applicator member in a direction towards the tissue-facing surface of the cartridge, wherein application of the load is configured to cause the at least one projection of the adjunct material to be at least partially received in a corresponding recess of the at least one recess formed in the cartridge to thereby cause the adjunct material to be releasably mated with the first jaw, and wherein the removable applicator member includes at least one applicator member projection facing the adjunct material and formed on the applicator member at a location thereof corresponding to a location of the at least one projection of the adjunct material.

13. The end effector of claim 12, wherein the at least one recess comprises, two or more recesses formed at a distal end of the cartridge and formed on opposite sides on the cutting element channel, and two or more recesses formed at a proximal end of the cartridge and formed on opposite sides of the cutting element channel.

14. The end effector of claim 12, wherein, when the removable applicator member is configured to apply the force to the adjunct material, the at least one applicator member projection is configured to cause the at least one projection of the adjunct material to be at least partially received in the corresponding recess.

15. The end effector of claim 12, further comprising a polymer attachment layer configured to be positioned between the first jaw and the adjunct material.

16. The end effector of claim 15, wherein the polymer attachment layer includes at least one second projection facing the adjunct material and formed on the polymer attachment layer at a location thereof corresponding to a location of the at least one projection of the adjunct material.

17. The end effector of claim 16, wherein, when the removable applicator member is configured to apply the force to the adjunct material and to the polymer attachment layer positioned between the first jaw and the adjunct material, the at least one applicator member projection is configured to cause the at least one projection of the adjunct material and the at least one second projection of the polymer attachment layer to be at least partially received in the corresponding recess.

18. The end effector of claim 12, wherein the at least one projection includes at least one longitudinal projection that extends between distal and proximal ends of the adjunct material.

19. The end effector of claim 18, wherein the at least one longitudinal projection has a mating feature formed thereon that is configured to be received within the corresponding recess, and wherein the at least one longitudinal projection is formed from at least partially flexible material such that, as the at least one longitudinal projection is received within the corresponding recess, the longitudinal projection is contracted due to the force being applied by the removable applicator member and then expanded to be fittingly received within the corresponding recess.

20. The end effector of claim 12, wherein the at least one projection comprises a plurality of discrete projections formed from an at least partially flowable material and having a changeable configuration such that, when the removable applicator member applies the force to the adjunct material to cause each of the discrete projections to be at least partially received within its corresponding recess, the configuration of each discrete projection that is at least partially received within its corresponding recess changes to conform to a configuration of its corresponding recess.

21. The end effector of claim 20, wherein each of the discrete projections is configured to separate from the adjunct material and remain within its corresponding recess after the staples are formed against the staple forming cavities to apply the adjunct material to a tissue clamped between the first and second jaws.

* * * * *